United States Patent
Dickerson et al.

(10) Patent No.: US 9,271,841 B2
(45) Date of Patent: Mar. 1, 2016

(54) BALL JOINT PROSTHESIS AND METHOD

(71) Applicant: Zimmer, Inc., Warsaw, IN (US)

(72) Inventors: Jeff Dickerson, Warsaw, IN (US); J. Craig Fryman, New Paris, IN (US); Donald L. Yakimicki, Warsaw, IN (US)

(73) Assignee: ZIMMER, INC., Warsaw, IN (US)

( * ) Notice: Subject to any disclaimer, the term of this patent is extended or adjusted under 35 U.S.C. 154(b) by 3 days.

(21) Appl. No.: 14/108,747

(22) Filed: Dec. 17, 2013

(65) Prior Publication Data

US 2014/0180424 A1    Jun. 26, 2014

Related U.S. Application Data

(60) Provisional application No. 61/740,105, filed on Dec. 20, 2012.

(51) Int. Cl.
| | |
|---|---|
| *A61F 2/30* | (2006.01) |
| *A61F 2/32* | (2006.01) |
| *A61F 2/40* | (2006.01) |
| *A61F 2/36* | (2006.01) |
| *A61F 2/38* | (2006.01) |

(52) U.S. Cl.
CPC .............. *A61F 2/4014* (2013.01); *A61F 2/3609* (2013.01); *A61F 2/30744* (2013.01); *A61F 2/38* (2013.01); *A61F 2002/30011* (2013.01); *A61F 2002/30014* (2013.01); *A61F 2002/30016* (2013.01); *A61F 2002/30332* (2013.01); *A61F 2002/30563* (2013.01); *A61F 2002/30581* (2013.01); *A61F 2002/30588* (2013.01); *A61F 2002/3611* (2013.01); *A61F 2002/3619* (2013.01); *A61F 2310/00395* (2013.01); *A61F 2310/00592* (2013.01)

(58) Field of Classification Search
CPC ........... A61F 2/36; A61F 2/3601; A61F 2/40; A61F 2/4003; A61F 2/4014
See application file for complete search history.

(56) References Cited

U.S. PATENT DOCUMENTS

| | | | |
|---|---|---|---|
| 5,282,861 A | 2/1994 | Kaplan | |
| 2004/0122524 A1 | 6/2004 | Hunter et al. | |
| 2006/0149386 A1* | 7/2006 | Clarke et al. | 623/18.12 |
| 2006/0247639 A1 | 11/2006 | Anderson | |
| 2007/0032877 A1 | 2/2007 | Whiteside | |
| 2008/0255674 A1 | 10/2008 | Rahaman et al. | |
| 2010/0121458 A1* | 5/2010 | Ledger et al. | 623/23.12 |
| 2010/0262144 A1* | 10/2010 | Kelman et al. | 606/62 |

* cited by examiner

*Primary Examiner* — Jason-Dennis Stewart
(74) *Attorney, Agent, or Firm* — Schwegman Lundberg & Woessner, P.A.

(57) ABSTRACT

A ball joint prosthesis can include a shell, having an outer articular surface of a first material and an open distal end, configured to receive a sealing receptacle. A volume of a second material, within the shell, can be more compressible than the first material. The ball joint prosthesis can have an effective compressibility that is intermediate between a compressibility of the first material and a compressibility of the second material.

20 Claims, 4 Drawing Sheets

BALL JOINT PROSTHESIS AND METHOD

CLAIM OF PRIORITY

This application claims the benefit of U.S. Provisional Patent Application Ser. No. 61/740,105, filed on Dec. 20, 2012, the benefit of priority of which is claimed hereby, and which is incorporated by reference herein in its entirety.

TECHNICAL FIELD

The present disclosure relates to composite bone joint prostheses and methods of manufacturing the same.

BACKGROUND

Prosthetic devices, such as prosthetic implants, can replace or augment body components or portions of body components that cannot be regenerated or are no longer functioning properly. Examples of prosthetic implants include heart valves, pacemakers, spinal implants, dental implants, breast implants, collagen for soft tissue augmentation, and orthopedic devices, such as artificial knee, hip, shoulder, and ankle joints.

Some prosthetic implants can include components that articulate to mimic the motion of a body component. For example, a humeral or femoral ball joint can be used in hip or shoulder arthroplasty procedures. Such components can include a biocompatible wear resistant material on an outer surface.

U.S. Patent Publication 2008/0255674 is directed toward a femoral head including an inner metal core bonded to a ceramic outer layer.

U.S. Patent Publication 2006/0247639 is directed toward composite spinal components formed of a polymeric material and at least one metal.

SUMMARY

The present inventor has recognized, among other things, that a prosthesis can include a plurality of materials to better mimic a body component or portion of a body component. For example, a humeral head prosthesis can include an outer articulating surface of a hardened material and an inner volume of a shock absorbing material to mimic characteristics of a humeral head body component. To better illustrate the variable ball joint prosthesis and related methods disclosed herein, a non-limiting list of examples is provided:

In Example 1, a ball joint prosthesis comprises a shell, comprising an outer articular surface of a first material and an open distal end, configured to receive a portion of a sealing receptacle. The ball joint prosthesis can include a volume of a second material, within the shell, that is more compressible than the first material, wherein the ball joint prosthesis has an effective compressibility that is intermediate between a compressibility of the first material and a compressibility of the second material.

In Example 2, the prosthesis of Example 1 is optionally configured such that the sealing receptacle, coupled to the first material, is configured to accept a portion of a prosthetic orthopedic stem to the ball joint prosthesis.

In Example 3, the prosthesis of Example 1 is optionally configured such that the sealing receptacle, included in or coupled to the volume of the second material, is configured to accept a portion of a prosthetic orthopedic stem to the ball joint prosthesis.

In Example 4, the prosthesis of anyone one or any combination of Examples 2 or 3 is optionally configured such that the sealing receptacle further comprises a back portion configured to be received within the volume of the second material and a front portion comprising a bore configured to accept at least the portion of the prosthetic orthopedic stem.

In Example 5, the prosthesis of Example 4 is optionally configured such that the front portion is flush with the open distal end.

In Example 6, the prosthesis of Example 5 is optionally configured such that the sealing receptacle is configured to threadably engage the first material.

In Example 7, the prosthesis of Example 4 is optionally configured such that the sealing receptacle further comprises a sealing rim configured to abut the outer articular surface to raise the front portion from the open distal end.

In Example 8, the prosthesis of any one or any combination of Examples 4-7 is optionally configured such that the bore is tapered or threaded.

In Example 9, the prosthesis of any one of or any combination of Examples 1-8 is optionally configured such that the sealing receptacle is formed of the first material.

In Example 10, the prosthesis of any one or any combination of Examples 1-9 is optionally configured such that the volume of the second material substantially fills the shell.

In Example 11, the prosthesis of any one or any combination of Examples 1-10 is optionally configured such that the volume of the second material is porous.

In Example 12, the prosthesis of any one or any combination of Examples 1-11 is optionally configured such that the volume of the second material includes trabecular metal.

In Example 13, the prosthesis of any one or any combination of Examples 1-12 is optionally configured such that the shell comprises trabecular metal.

In Example 14, the prosthesis of any one or any combination of Examples 1-13 is optionally configured such that the second material is a polymeric material.

In Example 15, the prosthesis of Example 14 is optionally configured such that the polymeric material is at least one of polyetheretherketone (PEEK), ultrahigh molecular weight polyethylene (UHMWPE), polyurethane, polycarbonateurethane, hydrogels, and combinations thereof.

In Example 16, the prosthesis of any one or any combination of Examples 1-15 is optionally configured such that the first material is a ceramic material.

In Example 17, the prosthesis of any one or any combination of Examples 1-16 is optionally configured such that the first material comprises a metallic material, including at least one of stainless steel, cobalt-chrome, and titanium.

In Example 18, the prosthesis of any one or any combination of Examples 1-17 is optionally configured such that the compressibility of the volume of the second material is within a specified threshold of a compressibility of bone to which the stem or shell is to be coupled.

In Example 19, the prosthesis of any one or any combination of Examples 1-18 is optionally configured such that a hardness of the volume of the second material is approximately between about Shore 20A to about Rockwell 140R.

In Example 20, the prosthesis of any one or any combination of Examples 1-19 is optionally configured such that the first material has a modulus of at least approximately 14,500 kilopounds per square inch (ksi).

In Example 21, the prosthesis of any one or any combination of Examples 1-20 is optionally configured such that the prosthesis comprises a femoral or humeral head.

In Example 22, the prosthesis of any one or any combination of Examples 1-21 is optionally configured such that the first material is bonded to the volume of the second material.

In Example 23, the prosthesis of any one or any combination of Examples 1-22 is optionally comprises the prosthetic orthopedic stem.

In Example 24, the prosthesis of any one or any combination of Examples 1-23 is optionally configured such that the shell is substantially spherical.

In Example 25, a method of making a ball joint prosthesis comprises providing a shell, the shell comprising an outer articular surface of a first material; and an open distal end, configured to receive a portion of a sealing receptacle. The method can further comprise providing a volume of a second material, within the shell, that is more compressible than the first material, wherein the ball joint prosthesis has an effective compressibility that is intermediate between a compressibility of the first material and the compressibility of the second material.

In Example 26, the method of Example 25 is optionally configured such that providing the volume of the second material comprises molding a polymeric material within the shell of the first material comprising a metal or ceramic.

In Example 27, the method of any one or any combination of Examples 25 or 26 is optionally configured such that wherein providing the volume of the second material comprises inserting a polymer foam within the shell of the first material, carbonizing the foam, and depositing a metal about the carbonized foam to form trabecular metal within the shell.

In Example 28, the method of any one or any combination of Examples 24-26 optionally further comprises machining a bore into the ball joint prosthesis to form the open distal end of the shell.

In Example 29, the method of Example 28 optionally further comprises inserting a portion of the tapered sealing receptacle into the bore and bonding the sealing receptacle to the ball joint prosthesis.

In Example 30, a ball joint prosthesis comprises a shell, including an outer articular surface of a first material and an open distal end, configured to receive a portion of a prosthetic orthopedic stem. The ball joint prosthesis further comprises a volume of a second material that substantially fills the shell, the second material more compressible than the first material and within a specified threshold of a compressibility of bone to which the prosthetic orthopedic stem or shell is to be coupled, wherein the ball joint prosthesis has an effective stiffness that is intermediate between a compressibility of the first material and a compressibility of the second material. A sealing receptacle is included in or coupled to the volume of the second material, wherein the sealing receptacle is configured to secure the prosthetic orthopedic stem to the ball joint prosthesis, the sealing receptacle including a back portion configured to be received within the volume of the second material and an front portion comprising a bore configured to secure the prosthetic orthopedic stem In Example 31, the ball joint prosthesis of Example 30 is optionally configured such that the second material is a fully cured solid material.

In Example 32, the ball joint prosthesis of Example 30 is optionally configured such that the second material is a viscous material configured to shift during an articulation event.

In Example 33, the ball joint prosthesis of any one or any combination of Examples 30-32 is optionally configured such that the second material includes a plurality of beads.

In Example 34, the ball joint prosthesis of any one or any combination of Examples 30-33 is optionally configured such that the second material is a thermal insulator configured to reduce temperature fluctuations of the ball joint prosthesis.

In Example 35, the ball joint prosthesis or method of any one or any combination of Examples 1-34 is optionally configured such that all elements or options recited are available to use or select from.

These and other examples and features of the present prosthetic implants and methods will be set forth in part in the following Detailed Description. This Summary is intended to provide non-limiting examples of the present subject matter—it is not intended to provide an exclusive or exhaustive explanation. The Detailed Description below is included to provide further information about the present prosthetic implants and methods.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present document.

DETAILED DESCRIPTION

The present disclosure relates generally to a ball joint prosthesis and related method. Generally, a ball joint prosthesis can include an outer surface configured to withstand articulating forces such as friction, stress, compression, or impact. For example, a ball joint prosthesis can be manufactured of a wear-resistant material, such as a metal or ceramic. Such materials are typically stiff solid materials that have relatively good wear and abrasion properties, but do not take into consideration the natural properties (e.g., stiffness/flexibility and compressibility) of the body component the prosthesis is meant to augment or replace. Other prosthesis components can be manufactured of a polymer, such as a material that is closer in stiffness to cartilage but lacks good wear or abrasion properties as a metal or ceramic. Examples according to the present disclosure include, a ball joint prosthesis having good wear or abrasion properties that more closely match the natural properties of the body component the prosthesis is meant to augment or replace.

Figure 1:
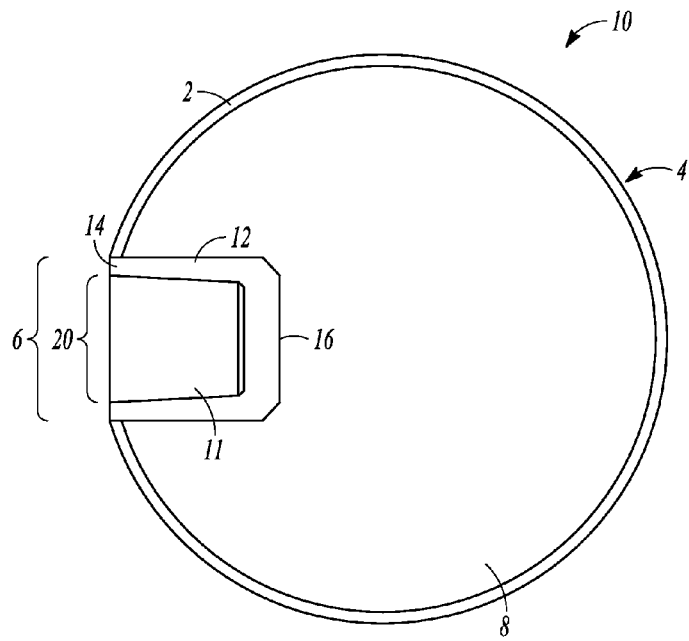
FIG. 1 illustrates a perspective view of a ball joint prosthesis of the present disclosure.

As shown in FIG. 1, a ball joint prosthesis 10 can include a shell 2 including an outer articulating surface 4 formed of a first material. In an example, the shell 2 can include a substantially spherical shell, such as any shape at least partially spherical in geometry, such as at least about ⅛ of a full sphere, ⅕ of a full sphere, ¼ of a full sphere, ⅓ of a full sphere, ½ of a full sphere, ⅜ of a full sphere, ⅔ of a full sphere, ⅘ of a full sphere, and ⅞ of a full sphere. Further examples can include non-spherical shells 2 for use in non-spherical articular joints, such as a knee or an ankle, among others. The ball joint prosthesis 10 can include any component of an implant that is configured to articulate, so as to mimic motion of a body component, such as a femoral or humeral head of an implant, a knee joint, or any small joint in the body. For example, a humeral head body component can articulate within a glenoid to form a glenohumeral joint to permit movement of a person's shoulder. The ball joint prosthesis 10 can replace the humeral head body component and can articulate within a glenoid to form a glenohumeral joint. In other embodiments, the ball joint prosthesis can be used in a total hip or shoulder replacement.

The outer articulating surface 4 can be formed of a first material. The first material can include any material configured to withstand forces such as blunt force, frictional wear, stress, temperature related fatigue, and the like, experienced during implant insertion, use or removal. The first material of the outer articulating surface 4 can exhibit strong material properties, such that it is durable enough to at least withstand normal loads or forces generated during one or more activities, including walking, running, standing, lifting, flexing, or jumping. The first material can have a relatively low frictional engagement of about 0.01 to about 0.7 with an implant or body component, such as during articulation. For example, the ball joint prosthesis 10 can be a femoral head configured to articulate within an acetabular cup of an implant with relatively low friction. Low frictional engagement can provide the benefit of ease of movement for a person, increased range of motion, mitigation of hot spots resulting from frictional forces, or improved durability of the ball joint prosthesis 10. The first material 2 can include metals, such as cobalt chrome, stainless steel, titanium or tantalum, or other ceramic type materials, such as alumina, zirconia, chromium carbide, chromium nitride, silicon carbide, silicon nitride, zirconium carbide, titanium carbide, tantalum carbide, or tungsten carbide or zirconium nitride.

The shell 2 can be of a specified thickness (~0.20 to 6.35 mm) of one or more layers of material, including at least the first material. For example, the shell 2 can be between about 0.008 inches to about 0.25 inches thick. The thickness of the shell 2 can be configured so that the shell 2 is rigid or deforms a specified amount under a specified force. For example, the first material can be a specified thickness to provide an articulating surface or can be a specified thickness to provide rigidity to the shell 2. In an example, the thickness of the shell 2 can be approximately consistent or can vary. The thickness of the shell 2 can be specified according to a stiffness of the one or more layers of material, including at least the first material, a proportion of the diameter of a second material, as a proportion of the diameter of the ball joint prosthesis, a use for the ball joint prosthesis 10, type or property of second material used, or desired effective characteristic of the ball joint prosthesis 10, such as effective compressibility, stiffness, or thermal property. The first material can have a modulus between about 10,000 kilopounds per square inch (ksi) to about 20,000 ksi. In an example, the first material can have a modulus of about 14,500 ksi.

A diameter of the shell 2 can be such that the ball joint prosthesis can closely fit within an implant cup or a body component. For example, the diameter of the shell 2 can be about 0.5 inches to about 2.5 inches. The diameter can be specified according to the body component the ball joint is designed to augment or replace. For example, the ball joint can be designed to a shell 2 diameter of approximately 1.0 inches to about 1.5 inches, so as to replace a femoral head of an individual. Further examples can include, a shell 2 diameter of approximately 2.5 inches to about 3.5 inches, such as in a hip replacement. Shoulder applications can include a shell 2 diameter of at least a portion of the shell 2 from about 1.5 inches to about 2.5 inches.

The shell 2 can include an open distal end 6 configured to receive a sealing receptacle 12. The open distal end 6 can be about 5%, about 10%, about 15%, about 25%, about 40%, about 50%, or any other percentage of a circumference of the shell 2 suitable to receive the sealing receptacle 12. The open distal end 6 can be of any geometric shape such as circular, rectangular, polygonal, star shaped, or any pattern configured to receive the sealing receptacle 12. In an example, the open distal end 6 can be configured such that the shell 2 has a profile of a circle with a wedge missing, as shown in FIG. 1. The open distal end 6 can include beveled edges, rounded edges, square edges, or the like.

The ball joint prosthesis 10 can include a volume of a second material 8, within the shell 2. The second material 8 can be more compressible than the first material. The second material 8 can be configured, either alone or in conjunction with the shell 2, to mimic compressibility of an interior volume of a body component, such as a femoral or humeral head, knee joint, or other small joint. The compressibility of the volume of the second material 8 can be within a specified threshold of a compressibility of bone to which the prosthetic stem or shell can be coupled. The volume of the second material 8 can have a softness of at least about Shore 20A, according to a durometer. In an example, the second material 8 can have a hardness of about Rockwell 140R, according to a durometer. The ball joint prosthesis 10 can have an effective compressibility that is intermediate between a compressibility of the first material and the compressibility of the second material 8.

The second material 8 can include any material more compressible than the first material. For example, the second material can include a porous material, such as tantalum or Trabecular Metal™ technology. Trabecular Metal™ technology is generally available from Zimmer®, Inc., of Warsaw, Ind. Trabecular Metal™ is a trademark of Zimmer® Technology, Inc. Such a material can be formed from a reticulated vitreous carbon foam substrate which is infiltrated and coated with a biocompatible metal, such as tantalum, etc., by a chemical vapor deposition ("CVD") process in the manner disclosed in detail in U.S. Pat. No. 5,282,861, the disclosure of which is incorporated herein by reference. Other metals such as niobium or alloys of tantalum and niobium with one another or with other metals can also be used.

The second material 8 can include a biocompatible polymeric or other plastic material including polyamide, polyphenylsulfone, polyethersulfone, polysulfone, polyketone, polyarylamide, polyetheretherketone (PEEK), polycarbonate, polystyrene, acrylonitrile butadiene styrene (ABS), acrylics, polyetherimide, polyimide, polyphenylsulfone, polymethoylmethacrylate, fiber filled variations of these polymers, amorphous polymeric material, ultrahigh molecular weight polyethylene (UHMWPE), polyurethane, polycarbonateurethane, hydrogels, such as polyvinylalcohol (PVA) or polyethylene glycol (PEG), combinations thereof, or various other biocompatible polymers. The volume of the second material 8 can substantially fill a cavity created by the shell 2, so as to be bonded to the shell 2 or not bonded to the shell 2. The second material 8 can include a substantially fully cured material, such that the first material and second material 8 can be bonded together, such as by an adhesive or the curing process. A substantially fully cured material can include bone cement. Diffusion bonding or CVD bonding can be used to bond the first material to the second material 8 if the second material 8 is metallic/ceramic. The first and second material can be bonded, such as by solvent bonding, use of adhesives, or molding, if, for example, the second material 8 is polymeric. In an example, the second material 8 can be cured within the volume of the shell 2, such that the curing of the second material can bond the second material to the shell 2. In an example, the second material can include a viscous material configured to shift during an articulation event, a plurality of beads sealed within the shell 2 by the sealing receptacle, or a thermal insulator configured to reduce temperature fluctuations of the ball joint prosthesis.

As shown in FIG. 1, at least a portion of a sealing receptacle 12 can be included in or coupled to the volume of the second material 8, so as to secure a portion of a prosthetic orthopedic stem (not shown) to the ball joint prosthesis 10. A back portion 16 of the sealing receptacle can be substantially surrounded by the second material 8. A front portion 14 of the sealing receptacle 12 can define a bore 20, such that a portion of the orthopedic stem can be received within the bore 20. The bore can be tapered, threaded, or can contain any other means configured to secure at least the portion of the orthopedic stem. In an example, the sealing receptacle 12 can be formed of a uniform material, such as the first material, the second material 8, or a third material. The third material can include porous, non-porous, metallic, ceramic, or polymeric materials described herein. The front portion 14, inner walls of the bore 20, and the back portion 16 can be formed of different materials. For example, at least a portion of the inner walls 11 of the bore 20 can be formed of the first material to aid in articulation of the orthopedic stem (not shown) within the bore 20, and the back portion 16 can be formed of the second material 8, so as to aid in bonding the sealing receptacle 12 with the bone joint prosthesis 10. Suitable biocompatible materials for the receptacle can include, for example, a metallic material such as at least one of a variety of stainless steel composites, titanium, chromium-cobalt, tantalum, or the like, or a non-metallic biocompatible material such as a biocompatible polymeric or other plastic material including polyamide, polyphenylsulfone, polyethersulfone, polysulfone, polyketone, polyarylamide, polyether ether ketone (PEEK), polycarbonate, polystyrene, acrylonitrile butadiene styrene (ABS), acrylics, polyetherimide, polyimide, polyphenylsulfone, polymethoylmethacrylate, fiber filled variations of these polymers, amorphous polymeric material, or various other biocompatible polymers.

As illustrated in FIG. 1, the sealing receptacle 12 can be placed within the volume of the second material 8, such that the front portion 14 is substantially flush with the outer articular surface 4. Such an example can include a bond between at least a portion of the sealing receptacle 12 and at least one of the first material and the volume of the second material 8. The receptacle 12 can be bonded, for example, with an adhesive, by diffusion bonding, by CVD bonding, or the like. In an example, the front portion 14 can be configured such that the sealing receptacle 12 press or snap fits in the ball joint prosthesis 10.

Figure 2:
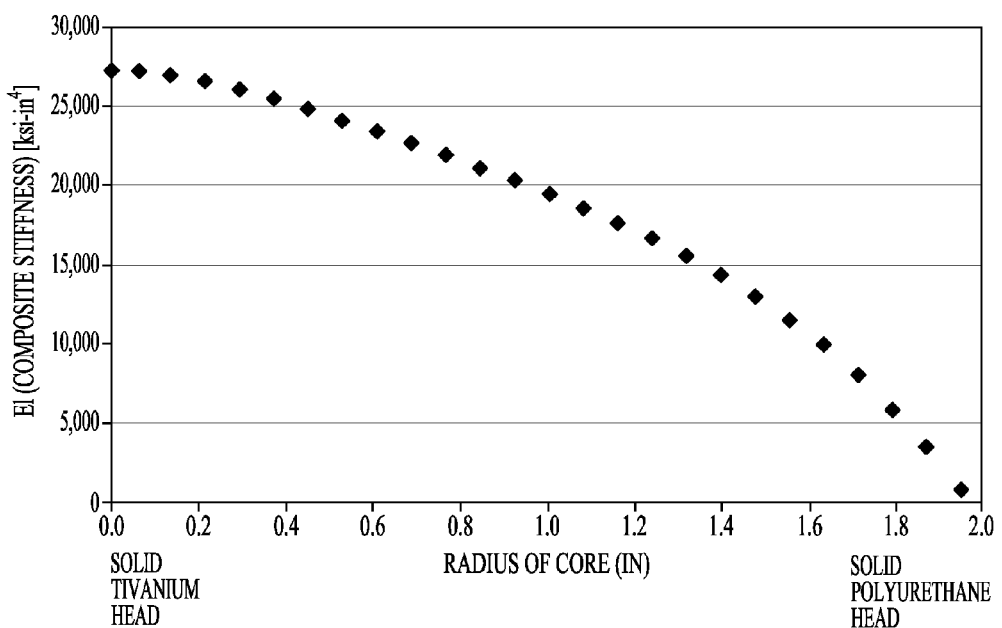
FIG. 2 is a plot of effective stiffness vs. volume of second material size in accordance with at least one example of the present disclosure.

FIG. 2 illustrates the effective stiffness of an approximately 2.0 inch diameter spherical ball joint prosthesis including a core of polyurethane encased in spherical titanium shell. In FIG. 2, the radius of the core and the thickness of the outer articular surface 4 vary, but the diameter of ball joint prosthesis remains constant. As can be seen in FIG. 2, a ball joint prosthesis formed of an approximately 2.0 inch diameter solid titanium hemisphere can have a composite stiffness of about 27,000 ksi-in$^4$, whereas an approximately 2.0 inch diameter titanium hemisphere constructed of a shell of 0.05 inch titanium over a core of polyurethane has an effective stiffness of approximately 730 ksi-in$^4$. By varying the thickness of the shell or core, the ball joint prosthesis 10 can be designed to meet a desired effective stiffness depending on where the ball joint prosthesis 10 will reside (e.g., shoulder or hip) and the particulars associated with the patient receiving the ball joint prosthesis (e.g., age, weight, or activity levels).

Figure 3A:
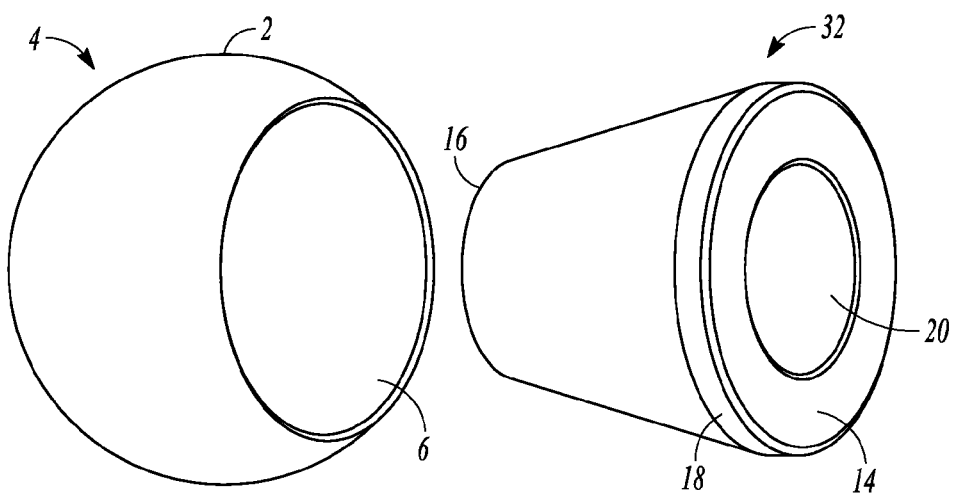
FIGS. 3A and 4A illustrate a deconstructed view of a ball joint prosthesis in accordance with at least one example of the present disclosure.
Figure 3B:
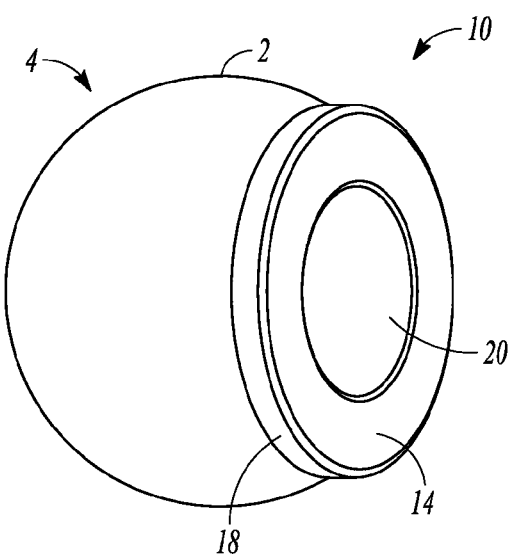
FIGS. 3B and 4B illustrate a perspective view of the ball joint prosthesis of FIGS. 3A and 4A, respectively.

FIG. 3A illustrates a deconstructed view of a ball joint prosthesis 10 according to at least one example of the present disclosure. FIG. 3B illustrates a perspective view of the ball joint prosthesis 10 of FIG. 3A. The sealing receptacle 32 includes a front portion 14, a back portion 16, and a bore 20, as described herein. Sealing receptacle 32 is similar to sealing receptacle 12 of FIG. 1 in that the back portion 16 is elongated from the front portion 14 such that the sealing receptacle substantially enters the cavity formed by the shell 2. Sealing receptacle 32 includes a rim 18 configured to abut the outer articular surface 4, such that the front portion 14 is raised from the open distal end 6. The front portion 14 can include at least one of a flat raised surface, a rounded raised surface, beveled edges, squared edges, or the like, based on the application of the ball joint prosthesis 10. The rim 18 can be configured to bond, such as by an adhesive, diffusion bonding, or CVD bonding, to the shell 2. Benefits of the example illustrated in FIG. 3 can include adding offset to the heads for better anatomic alignment, as well as providing a more accessible location to bond receptacle 32 to shell 2.

Figure 4A:
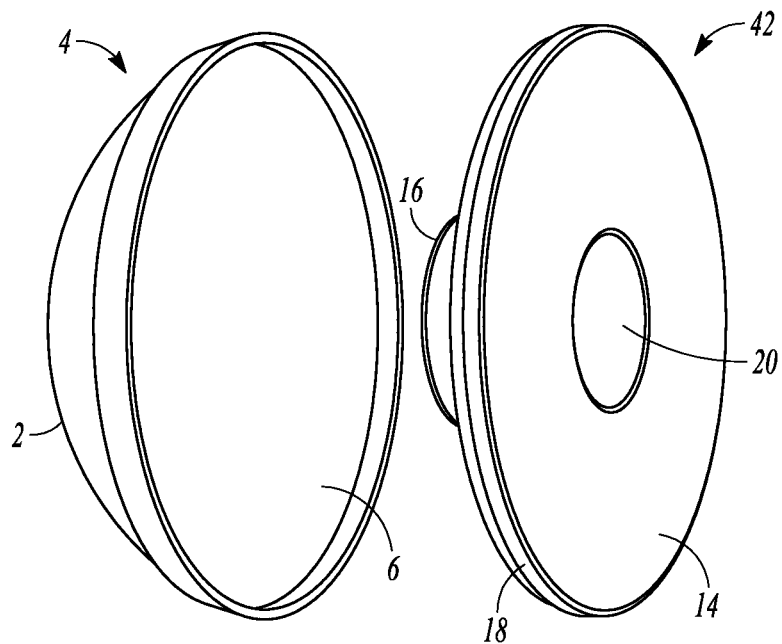
Figure 4B:
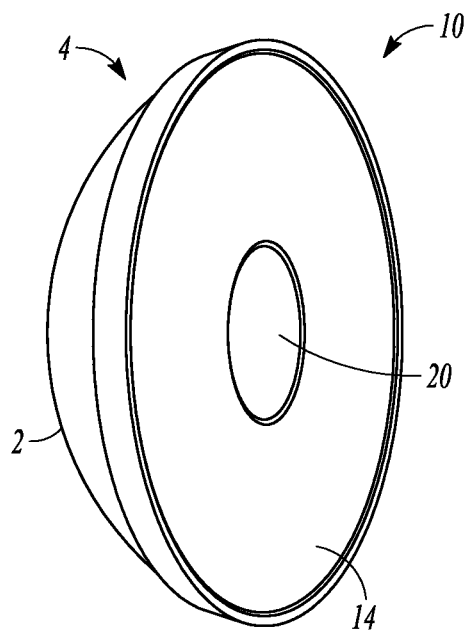

FIG. 4A illustrates a deconstructed view of a ball joint prosthesis 10 according to at least one example of the present disclosure. FIG. 4B illustrates a perspective view of the ball joint prosthesis 10 of FIG. 4A. Sealing receptacle 42 is configured to couple to the shell 2. For example, the rim 48 can include at least one exterior thread and the shell 2 can include at least one interior thread, such that the sealing receptacle 42 can threadably engage the shell 2. The rim 48 can be configured to bond, such as by an adhesive, diffusion bonding, or CVD bonding, to the shell 2. Such an example can configure the front portion 14 substantially flush with the open distal end 6.

Figure 5:
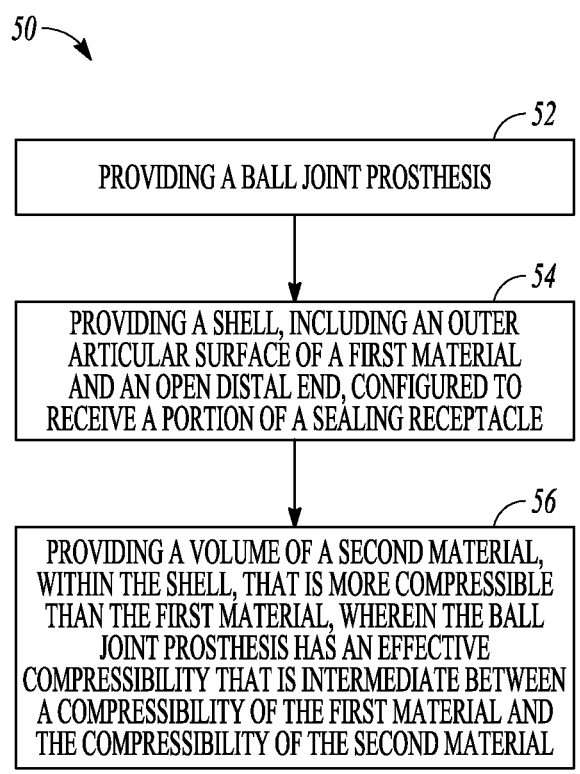
FIG. 5 is a flow chart of the method steps for providing a ball joint prosthesis in accordance with of the present disclosure.

FIG. 5 illustrates a method 50 for manufacturing a ball joint prosthesis according to the present description. At 52, a ball joint prosthesis is provided. At 54, a shell, including an outer articular surface of a first material and an open distal end, configured to receive a portion of a sealing receptacle, can be provided.

At 56, a volume of a second material is provided within the shell, wherein the second material can be more compressible than the first material. The ball joint prosthesis has an effective compressibility that is intermediate between a compressibility of the first material and the compressibility of the second material. In an example, providing the second material can include a polymeric material within the shell of the first material, the first material comprising a metal or ceramic, as described herein. Providing the second material can include inserting a polymer foam within the shell of the first material, carbonizing the foam, and depositing a metal about the carbonized foam to form a trabecular metal within the shell. In an example, providing the second material can include injecting, pouring (liquid or solid, in, e.g., powder form), or otherwise providing a liquid or solid material that can be made to solidify (e.g., cure) by methods known in the art (e.g., heating, chemical reaction, or irradiation). For example, the sealing receptacle can include an orifice or a self-sealing orifice on the back portion, such that a syringe or other delivery device can provide the second material within the shell. Further, the providing the second material can include providing a solid second material, such as solid polymer particles, within the shell.

The method 50 can include machining an open distal end into the ball joint prosthesis. The open distal end can include any style of edges. Further, the open distal end can be machined to a specified depth, based, for example, on the sealing receptacle, the use of the ball joint prosthesis, the first material, the second material, or combinations thereof. The cavity created by the machining can be tapered or straight. For example, the open distal end can be formed in a hollow sphere, such that machining the surface of the sphere can form the open distal end and the shell. Further, a small opening bored into the spherical shell, such that the second material can be inserted into the cavity of the spherical shell, allowed to cure, and the shell with the volume of cured second material can be machined to form the shell. In another example, a layer of the first material can be bonded or diffused to a volume of second material. The bonded materials can then be machined to form the shell including the open distal end. The method 50 can include inserting a portion of the tapered sealing receptacle into the bore and bonding the sealing receptacle to ball joint prosthesis. The sealing receptacle can be bonded to the ball joint prosthesis as described herein.

EXAMPLE

The present disclosure can be better understood by reference to the following examples which are offered by way of illustration. The present disclosure is not limited to the examples given herein.

Example 1

Ball Joint Prosthesis Construction

This example illustrates a variety of materials can be used as the first and second material within the ball joint prosthesis 10 to achieve a range of compressive forces.

A variety of 1.5 inch diameter hemispherical cores were tested in within a 1.5 inch titanium hemispherical shell formed from 0.016 inch thick sheet metal. Solid Cobalt Chrome and Ti-6Al-4V hemispherical samples were also tested. Each core-shell combination was loaded up to 500 lb-f at a rate of 50 lb-f per second on an Instron mechanical test machine. Table 1 summarizes the results.

TABLE 1

Compressive Stiffness Results

| Material Combination | Stiffness (lbf/in) | Standard Deviation (n = 5) |
| --- | --- | --- |
| Solid Titanium (Ti) | 35,896 | 247 |
| Solid Cobalt Chrome | 36,233 | 278 |
| Bone Cement Core in Titanium Shell | 32,866 | 328 |
| Silicone Rubber Core in Titanium Shell | 29,099 | 288 |
| Bone Cement Core in Titanium Shell | 32,866 | 328 |
| UHMWPE Core in Titanium Shell | 31,506 | 237 |

As illustrated, the bone joint prosthesis can use a variety of materials to obtain a desired effective compressive force of the ball joint prosthesis.

The above Detailed Description includes references to the accompanying drawings, which form a part of the Detailed Description. The drawings show, by way of illustration, specific embodiments in which the present bone joint prostheses and methods can be practiced. These embodiments are also referred to herein as "examples." While certain examples are shown and described with respect to a femoral head or a humeral head, it is to be appreciated that the present disclosure is equally applicable to both the femoral and humeral heads, as well as knee joints, small joints, and a variety of other prosthesis intended to replace a body component. All examples can also be used in partial or total bone component replacement procedures.

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In the event of inconsistent usages between this document and any document so incorporated by reference, the usage in this document controls.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, "front" refers to a direction generally toward the front of a patient, "back" refers to a direction generally toward the back of the patient, "medial" refers to a direction generally toward the middle of the patient, and "lateral" refers to a direction generally toward the side of the patient. In this document, the phrase "front/back direction" is used to include a front to back direction or a back to front direction.

In the appended claims, the terms "including" and "in which" are used as the plain-English equivalents of the respective terms "comprising" and "wherein." The terms "including" and "comprising" are open-ended, that is, a system, kit, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A ball joint prosthesis, comprising:
    a shell, comprising:
        an outer articular surface of a first material having a first compressibility; and
        an open distal end, configured to receive a portion of a sealing receptacle; and
    a volume of a second material, within the shell, the second material having a second compressibility that is greater than the first compressibility of the first material,
    wherein the sealing receptacle is coupled to the first material or formed of the first material, and is configured to accept a portion of a prosthetic orthopedic stem to the ball joint prosthesis, wherein the ball joint prosthesis has an effective compressibility that is intermediate between the first compressibility of the first material and the second compressibility of the second material.

2. The ball joint prosthesis of claim 1, wherein the volume of the second material is porous.

3. The ball joint prosthesis of claim 1, wherein the second material is a polymeric material including at least one of polyetheretherketone (PEEK), ultrahigh molecular weight polyethylene (UHMWPE), polyurethane, polycarbonateurethane, hydrogels, and combinations thereof.

4. The ball joint prosthesis of claim 1, wherein the first material is a ceramic material.

5. The ball joint prosthesis of claim 1, wherein the first material comprises a metallic material, including at least one of stainless steel, cobalt-chrome, and titanium.

6. The ball joint prosthesis of claim 1, wherein the second compressibility of the volume of the second material is within a specified threshold of a compressibility of bone to which the stem or shell is to be coupled.

7. The ball joint prosthesis of claim 1, wherein a hardness of the volume of the second material is between approximately about Shore 20A to about Rockwell 140R.

8. The ball joint prosthesis of one claim 1, wherein the first material has a modulus of at least approximately 14,500 kilopound per square inch (ksi).

9. A ball joint prosthesis, comprising:
a shell, comprising:
an outer articular surface of a first material having a first compressibility; and
an open distal end, configured to receive a portion of a sealing receptacle; and
a volume of a second material, within the shell, the second material having a second compressibility that is greater than the first compressibility of the first material,
wherein the sealing receptacle is included in or coupled to the volume of the second material, and is configured to accept a portion of a prosthetic orthopedic stem to the ball joint prosthesis, and
wherein the ball joint prosthesis has an effective compressibility that is intermediate between the first compressibility of the first material and the second compressibility of the second material.

10. The ball joint prosthesis of claim 9, wherein the sealing receptacle comprises a back portion configured to be received within the volume of the second material and a front portion comprising a bore configured to accept at least the portion of the prosthetic orthopedic stem.

11. The ball joint prosthesis of claim 10, wherein the sealing receptacle further comprises a sealing rim configured to abut the outer articular surface to raise the front portion from the open distal end.

12. The ball joint prosthesis of claim 10, wherein the bore is tapered or threaded.

13. The ball joint prosthesis of claim 9, wherein the second material is a polymeric material including at least one of polyetheretherketone (PEEK), ultrahigh molecular weight polyethylene (UHMWPE), polyurethane, polycarbonateurethane, hydrogels, and combinations thereof.

14. The ball joint prosthesis of claim 9, wherein the first material is a ceramic material.

15. The ball joint prosthesis of claim 9, wherein the second compressibility of the volume of the second material is within a specified threshold of a compressibility of bone to which the stem or shell is to be coupled.

16. The ball joint prosthesis of claim 9, wherein a hardness of the volume of the second material is between approximately about Shore 20A to about Rockwell 140R.

17. The ball joint prosthesis of claim 9, wherein the first material has a modulus of at least approximately 14,500 kilopound per square inch (ksi).

18. A ball joint prosthesis, comprising:
a shell, including:
an outer articular surface of a first material; and
an open distal end, configured to receive a portion of a prosthetic orthopedic stem;
a volume of a second material that substantially fills the shell, the second material more compressible than the first material and within a specified threshold of a compressibility of bone to which the prosthetic orthopedic stem or shell is to be coupled;
wherein the ball joint prosthesis has an effective stiffness that is intermediate between a compressibility of the first material and a compressibility of the second material; and
a sealing receptacle, included in or coupled to the volume of the second material, the sealing receptacle configured to secure the prosthetic orthopedic stem to the ball joint prosthesis, the sealing receptacle including a back portion configured to be received within the volume of the second material and an front portion comprising a bore configured to secure the prosthetic orthopedic stem.

19. The ball joint prosthesis of claim 18, wherein the second material is a fully cured solid material.

20. The ball joint prosthesis of claim 18, wherein the second material is a viscous material configured to shift during an articulation event.

* * * * *